(12) United States Patent
Vu et al.

(10) Patent No.: US 11,339,108 B2
(45) Date of Patent: May 24, 2022

(54) ACETONE RECOVERY AND PURIFICATION

(71) Applicants: Truc Van Vu, Houston, TX (US); Eric Wing-Tak Wong, Houston, TX (US); Paul Isaac Damin, Kingwood, TX (US); Ravi Shanker Sahu, Gurgaon (IN)

(72) Inventors: Truc Van Vu, Houston, TX (US); Eric Wing-Tak Wong, Houston, TX (US); Paul Isaac Damin, Kingwood, TX (US); Ravi Shanker Sahu, Gurgaon (IN)

(73) Assignee: KELLOG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 17/351,520

(22) Filed: Jun. 18, 2021

(65) Prior Publication Data

US 2021/0395180 A1 Dec. 23, 2021

(51) Int. Cl.
*C07C 45/82* (2006.01)
*C07C 45/85* (2006.01)

(52) U.S. Cl.
CPC .................. *C07C 45/85* (2013.01)

(58) Field of Classification Search
CPC ................ C07C 45/82; C07C 45/85
See application file for complete search history.

(56) References Cited

U.S. PATENT DOCUMENTS

| | | | |
|---|---|---|---|
| 2,986,583 A | 5/1961 | Robbers et al. | |
| 4,340,447 A | 7/1982 | Laverick et al. | |
| 5,371,305 A | 12/1994 | Hood | |
| 6,307,112 B1 | 10/2001 | Weber et al. | |
| 6,657,087 B2 | 12/2003 | Weber et al. | |
| 7,141,701 B1 | 11/2006 | Schmidt et al. | |
| 8,697,917 B2 | 4/2014 | Wilks et al. | |
| 8,889,915 B2 | 11/2014 | Vu et al. | |
| 2003/0088129 A1 | 5/2003 | Marshall, Jr. et al. | |

FOREIGN PATENT DOCUMENTS

WO 2004009522 A1 1/2004

OTHER PUBLICATIONS

KBR Phenol For McGraw-Hill, KBR Phenol Process, KBR Phenol—Handbook of Petrochemical Processes—McGraw-Hill, Feb. 2004; 22 pages.

International Search Report and Written Opinion dated Sep. 27, 2021 received for International Application No. PCT/US2021/038025 filed Jun. 18, 2021 (14 pages).

*Primary Examiner* — Sikarl A Witherspoon
(74) *Attorney, Agent, or Firm* — Gary M. Machetta

(57) ABSTRACT

Methods and systems for preparing acetone from cumene hydroperoxide (CHP) are disclosed. The disclosed methods involve cleaving CHP to form a cleavage product stream. In some embodiments, the cleavage product stream is separated into an overhead stream and a bottoms stream. The bottoms stream is neutralized, washed and then treated in a crude acetone column to provide a crude acetone stream. The overhead stream of the cleavage product is flashed forward in the process, bypassing the neutralization, washing, and crude acetone column and is then combined with the crude acetone stream. The combined acetone streams are provided to an acetone product column. According to some embodiments, the acetone product column comprises a side draw for obtaining a recycle acetone stream, which is recycled to the cleavage reactor(s). The recycle acetone side draw may be located lower on the acetone product column than the point from which product acetone is obtained. The disclosed methods increase the efficiency of the process.

19 Claims, 2 Drawing Sheets

ACETONE RECOVERY AND PURIFICATION

CROSS REFERENCE TO RELATED APPLICATIONS

The present application claims priority to U.S. Provisional Patent Application Ser. No. 63/041,465, filed Jun. 19, 2020, the contents of which are incorporated herein by reference.

FIELD OF THE INVENTION

This application relates to methods and systems for producing acetone from cumene. More specifically, embodiments relate to improving the efficiency of acetone recovery.

INTRODUCTION

Phenol and acetone are produced in various processes, the most common of which is known variously as the Hock Process, the Hock and Lang Process, or the cumene-to-phenol process, among others. This process begins with the oxidation of cumene (isopropyl benzene) to form cumene hydro-peroxide (CHP). The CHP is then cleaved in the presence of an acid catalyst to form a phenol, acetone, and/or alpha-methyl styrene ("AMS") mixture. The mixture is subsequently neutralized and fractionated to recover the end-products phenol, acetone, and/or AMS.

While such processes have been used for decades, there is a continued need for optimizing the efficiency of product recovery in such processes.

SUMMARY

Disclosed herein is a method of producing acetone, the method comprising: (i) cleaving cumene hydroperoxide (CHP) in at least one cleavage reactor to form a cleavage product stream, (ii) separating the cleavage product stream into an overhead stream and a bottoms stream, (iii) separating the bottoms stream in a crude acetone column to provide a phenol-rich stream and an acetone-rich stream, (iv) feeding both the overhead stream of step (ii) and the acetone-rich stream of step (iii) to an acetone product column, and (v) obtaining product acetone from the acetone product column. According to some embodiments, the at least one cleavage reactor comprises a first stage cleavage reactor and a second stage cleavage reactor, and cleaving CHP comprises: providing the CHP to the first stage cleavage reactor, contacting the CHP with an acid catalyst, recycled acetone, and water to form a first stage cleavage reactor product, providing the first stage cleavage reactor product to the second stage cleavage reactor, and obtaining the cleavage product stream as effluent from the second stage cleavage reactor. According to some embodiments, separating the cleavage product stream into an overhead stream and a bottoms stream comprises flashing the cleavage product stream in a flash drum to provide the overhead stream from the flash drum. According to some embodiments, the flash drum operates at a pressure of about 90 kPa to about 190 kPa. According to some embodiments, the overhead stream from the flash drum comprises about 60 volume % to about 75 volume % acetone. According to some embodiments, the method further comprises cooling the bottoms stream of step (ii). According to some embodiments, the method further comprises neutralizing the bottoms stream of step (ii). According to some embodiments, feeding both the overhead stream of step (ii) and the acetone-rich stream of step (iii) to an acetone product column comprises combining the overhead stream of step (ii) with the acetone-rich stream of step (iii) to form a combined stream and feeding the combined stream to the acetone product column. According to some embodiments, the crude acetone column comprises a condenser and wherein combining the overhead stream of step (ii) with the acetone-rich stream of step (iii) comprises feeding the overhead stream of step (ii) to the condenser. According to some embodiments, the method further comprises recycling recycle acetone from the acetone product column to a cleavage reactor that is used to perform step (i). According to some embodiments, the acetone product column comprises a first side draw from which the product acetone is obtained and a second side draw from which the recycle acetone is obtained. According to some embodiments, the second side draw is located below the first side draw.

Also disclosed herein is a method of producing acetone, the method comprising: (i) cleaving cumene hydroperoxide (CHP) in at least one cleavage reactor to form a cleavage product stream, (ii) treating at least a first portion of the cleavage product stream to wash and neutralize the first portion of the cleavage product stream, (iii) separating the first portion of the cleavage product stream in a crude acetone column to provide a phenol-rich stream and an acetone-rich stream, (iv) feeding the acetone-rich stream of step (iii) to an acetone product column, and (v) obtaining product acetone from a first side draw of the acetone product column and obtaining recycle acetone from a second side draw of the acetone product column. According to some embodiments, the second side draw is below the first side draw. According to some embodiments, the at least one cleavage reactor comprises a first cleavage reactor and a second cleavage reactor. According to some embodiments, the method further comprises recycling the recycle acetone to the second cleavage reactor. According to some embodiments, recycling the recycle acetone to the second cleavage reactor comprises recycling an amount of acetone that has a weight ratio of acetone to CHP of about 0.05 to about 0.25 based on the CHP provided to the at least one cleavage reactor. According to some embodiments, the method further comprises, prior to step (ii), flashing the cleavage product in a flash drum to provide the first portion of the cleavage product stream as a bottom stream from the flash drum and to provide an overhead stream. According to some embodiments, the method further comprises flashing the overhead stream forward downstream of the crude acetone column.

DETAILED DESCRIPTION

Figure 1:
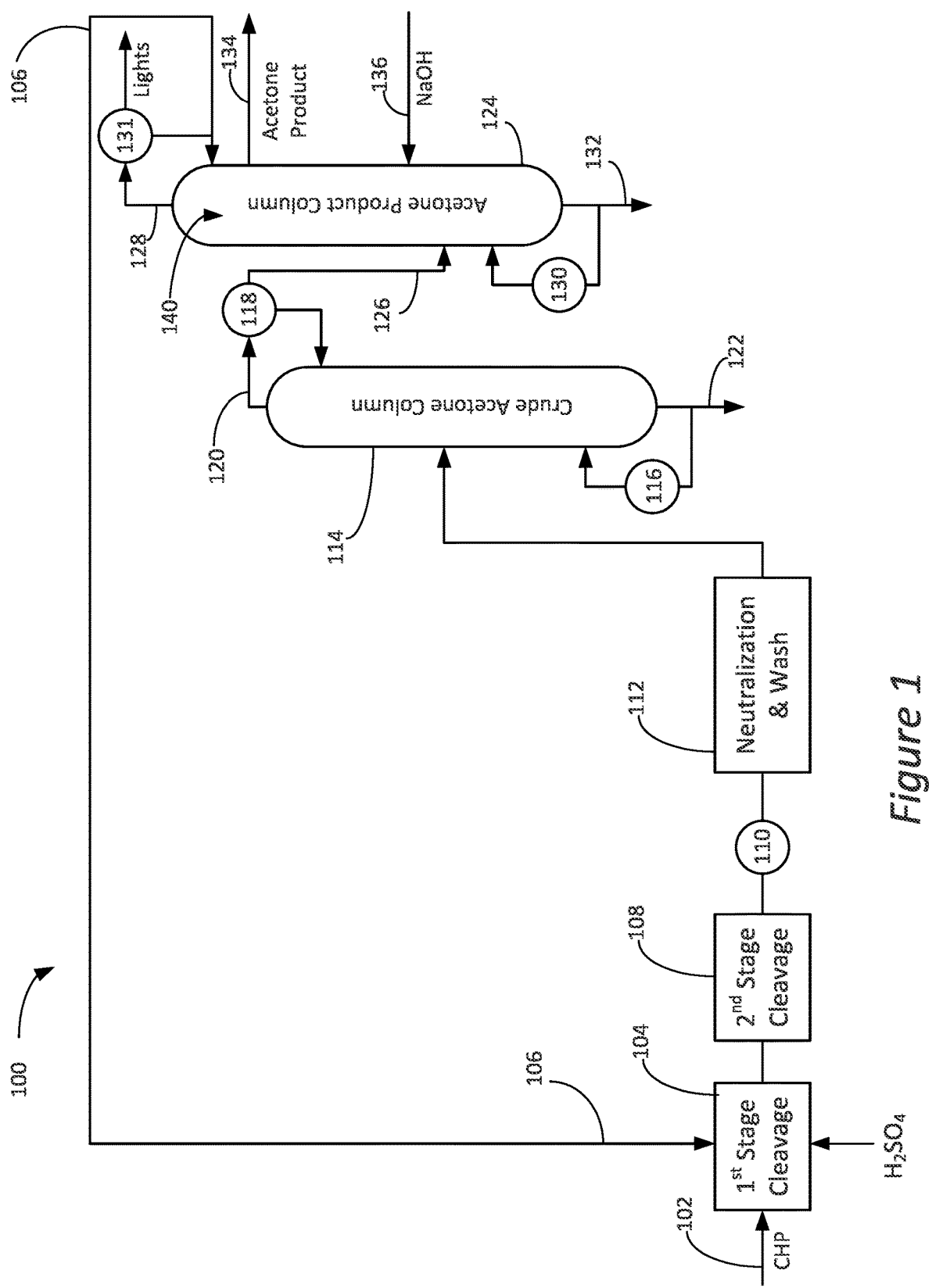
FIG. 1 shows an embodiment of a system for producing acetone and phenol from cumene hydroperoxide (CHP).

FIG. 1 illustrates a system 100 for producing acetone and phenol from cumene hydroperoxide (CHP). Concentrated CHP enters the system via line 102. The concentration of the CHP in line 102 may be about 65-90 wt. %, and is more typically about 80-85 wt. %, for example to about 82 wt. %. The CHP may be produced by the oxidation of cumene, for example, as described in U.S. Pat. No. 8,697,917, the entire contents of which are incorporated herein by reference. The oxidation product from the cumene oxidation (not shown) comprises CHP and may also comprise one or more of alpha-methyl styrene (AMS), dimethyl benzyl alcohol (DMBA), and/or acetophenone (ACP).

The concentrated CHP is provided to one or two cleavage reactors in series, for example, as described in U.S. Pat. No. 5,371,305. In the illustrated system 100, two cleavage reactors in series are illustrated. The CHP is provided to a first cleavage reactor 104, where it undergoes acid-catalyzed cleavage. The acid catalyst may be sulfuric acid ($H_2SO_4$), for example. In the illustrated embodiment, the first cleavage reactor may be a back-mixed reactor, for example, and operate between 50° C. and 80° C. In the first cleavage reactor, CHP partially reacts in two reactions, i) CHP cleaved to form phenol and acetone, and ii) CHP partially reacts with DMBA in an equilibrium reaction to give an intermediate product dicumyl peroxide (DCP) and water. DMBA is partially dehydrated to AMS, which reacts in consecutive reactions with phenol to high-boiling cumylphenols. AMS can also form high-boiling point dimers. Additional byproducts can also produce, such as hydroxyacetone (HA), 2-methylbenzofurane (2-MBF), and mesityl oxide (MO). The cleavage reaction is highly exothermic thus, recycled acetone may be provided to the cleavage reactor(s) to maintain the proper dilution, thereby minimizing the formation of undesirable by-products. In the illustrated embodiment, recycled purified acetone is provided to the first cleavage reactor via line 106. Water may also be added for optimum cleavage yields.

In the illustrated embodiment, the product of the first cleavage reactor 104 is fed to a second cleavage reactor 108 where three main reactions take place: i) residual CHP from first cleavage reactor cleaves to phenol and acetone, ii) dehydration of residual DMBA from first cleavage reactor to AMS, and iii) conversion of DCP to AMS, phenol, and acetone. The second stage cleavage reactor may be a plug flow reactor, for example, at temperatures about 105° C. to 145° C., and may be steam heated.

In the illustrated system 100, the cleavage product from the second cleavage reactor 108 is cooled using cooler 110 and directed to one or more neutralization and wash units 112. The cleavage effluent contains sulfuric acid used as catalyst for the cleavage reaction. To avoid corrosion problems in the downstream equipment, the acids must be extracted and neutralized using one or more bases, such as sodium hydroxide and/or one or more salt solutions. For example, the salt solution can be or include sodium phenate. The salt solution can reduce or stop any continuing cleavage reactions in the cleavage product. Accordingly, the neutralization and wash units 112 can produce a neutralized cleavage product. However, in the improved embodiments described below, the cleavage product is treated differently, as will be described.

The steps (i.e., acetone fractionation) following cleavage and neutralization are primarily aimed towards purification of products (acetone and phenol) and recovery of by-products and recyclable cumene. The acetone fractionation system serves the purpose of (1) crude separation of lights and heavies in the fractionation feed and (2) purification of acetone product. The organic effluent from the neutralization unit(s) 112 flows to a first distillation column, referred to herein as the crude acetone column (CAC) 114. The function of the CAC is to split the neutralization product into a phenol fraction and an acetone fraction. Aspects of a CAC are described in U.S. Pat. No. 8,889,915, the entire contents of which are incorporated herein by reference. The vapor distillate (line 120) contains acetone, water, cumene, AMS, small amounts of phenol, and other light materials in the feed. The CAC may be equipped with a CAC reboiler 116 and a CAC condenser 118. The CAC reboiler 116 may be a forced circulation type exchanger heated by high-pressure steam, for example. The phenol-rich bottom material (line 122) may be directed to a phenol fractionation unit (not shown). The overhead vapor (line 120) is partially condensed in the CAC condenser 118. The condensed liquid is returned to the CAC 114, while the vapor distillate is sent to a second distillation column, referred to herein as the acetone product column (APC) 124 via line 126.

The purpose of the APC 124 is to remove light ends (primarily acetaldehyde, via line 128) from acetone product and to separate acetone from water, cumene, AMS, and other heavy organics. Aspects of an APC are described in U.S. Pat. No. 4,340,447, the contents of which are incorporated by reference. The APC is equipped with an APC reboiler 130 and an APC condenser 131. The APC reboiler 130 may be fed from a liquid trap out of the bottom tray of the APC 124 and a re-circulation stream from the bottom of the column, and may heated by low-pressure steam.

An interior volume 140 of the APC 124 can be empty, partially filled, or completely filled with one or more fill materials (not shown). Illustrative fill materials can include, but are not limited to, trays, packing, or combinations thereof. As used herein, the term "trays' can include, but is not limited to, one or more types of trays that can improve the contact between gas and liquid phases within APC 124. Illustrative trays can include, but are not limited to perforated trays, sieve trays, bubble cap trays, floating valve trays, fixed valve trays, cartridge trays, dual flow trays, baffle trays, shower deck trays, chimney trays, slit trays, or any combination thereof. As used herein, the term "packing material' or "packing can include, but is not limited one or more types of structured and/or random shaped material disposed within APC 124. The packing material can increase the effective surface area within APC 124, which can improve the mass transfer between liquid and gas phases within APC 124. The packing material can be made of any suitable material, for example metals, non-metals, polymers, ceramics, glasses, or any combination thereof. Illustrative examples of random packing material can include, but is not limited to, Raschig rings, NeXRing™, Nutter Rings™, I-Rings™, C-Rings™, P-Rings™, R-Rings™ and S-Rings™, Intalox® ULTRA, IMTP®, HY-PAK®, CASCADE MINI RINGS®, FLEXIRING®, AHPP SaddleRings, Pall rings, SuperBlend™ 2-Pac, or any combination thereof. Illustrative examples of commercially available structured packing can include, but are not limited to, structured packing, corrugated sheets, crimped sheets, gauzes, grids, wire mesh, or any combination thereof. The fill material, can improve mass transfer and/or separation of a multi-component fluid. The fill material and/or the fill pattern in the interior Volume 140 can include one or more structured and/or random packed materials. Two or more types of fill material can be disposed within the interior volume 126. The APC 124 can be made of one or more metallic materials physically and chemically compatible with the temperature, pressure, and contents of APC 124. Suitable metallic materials can include, but are not limited to ferrous alloys including carbon and stainless steels such as cladded carbon Steel and 304 and 316 stainless steels, and duplex stainless steel and combination of these metallic materials. Further, the APC 124 can be operated at a pressure temperature ranging from a low of about 40 kPa, about 50 kPa, or about 60 kPa, to a high of about 80 kPa, about 90 kPa, or about 100 kPa.

The net bottoms stream 132 from the APC 124 may be fed to a crude AMS was section (not shown). Product acetone may be obtained from a side draw 134. A portion of the APC 124 reflux from the reflux condenser 131 may be recycled to the cleavage reactor section via line 106, for example, to the first cleavage reactor 104, as mentioned above. Note that the recycle acetone (line 016) could also be taken as a portions of the acetone product side draw 134. The amount of recycled acetone may be determined as a ratio based on the feed of CHP to the cleavage reactor. For example, the amount of acetone recycled to the cleavage reactor(s) has an acetone to CHP weight ratio may be about 0.05 to about 0.25 based on the feed of CHP to the cleavage reactor(s).

The APC 124 may be provided with one or more caustic addition points 136 for the addition of caustic materials, such as sodium hydroxide (NaOH). For example, the caustic addition point(s) 136 may be between the feed stream 126 and the product side draw 134.

It will be appreciated that some aspects and equipment of the system 100 that are not particularly relevant to this disclosure but that are implemented in the actual operation of such a system are not mentioned here. Such aspects and equipment are known in the art and may be described in the above-incorporated references.

Figure 2:
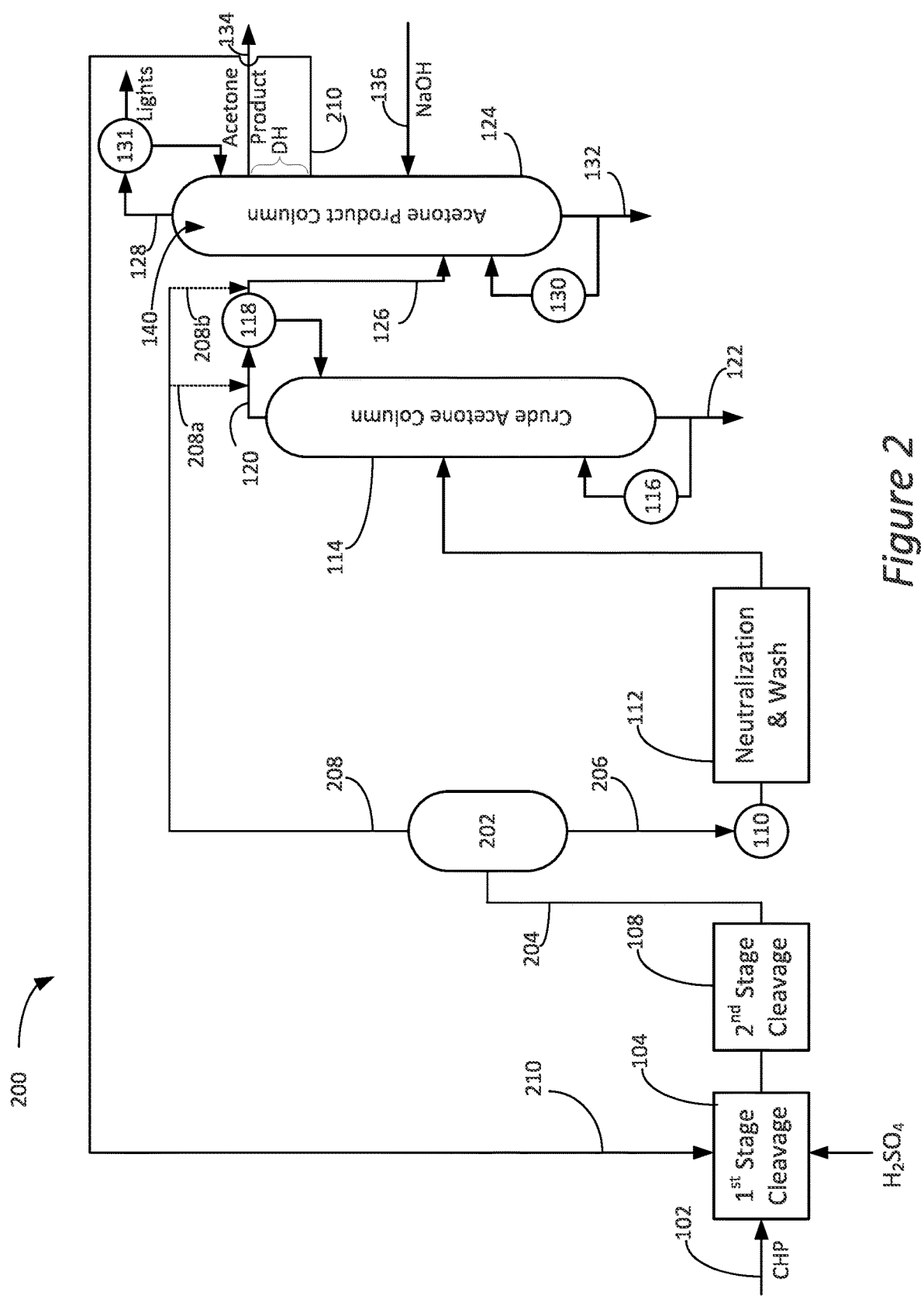
FIG. 2 shows an embodiment of an improved system for producing acetone and phenol from cumene hydroperoxide (CHP).

The inventors have discovered that the efficiency of the system 100 can be improved. FIG. 2 illustrates a system 200 for producing acetone and/or phenol from CHP that is similar to system 100 (FIG. 1) in some respects, but that includes several improved features. A first additional aspect of the system 200 is a flash drum 202, which is equipped to receive effluent from the cleavage reactor stage, for example from the second cleavage reactor 108. Recall from the discussion above, that the second cleavage reactor operates at an elevated temperature, for example, ranging from a low of about 105° C., about 110° C., about 115° C., to a high of about 135° C., about 140° C., or about 145° C. In the system 200, the effluent (containing acetone vapor) is provided to the flash drum 202 via line 204. The flash drum may operate at a pressure ranging from a low of about 90 kPa, or about 100 kPa, to a high of about 180 kPa, or about 190 kPa. The liquid bottoms contained in the flash drum 202 is provided to the neutralization cooler 110 via line 206. The acetone-containing vapor from the flash drum 202 is "flashed forward" in the process via line 208, bypassing the neutralization unit 112 and the CAC 114. This acetone-containing vapor has a temperature ranging from a low of about 85° C., or about 90° C., to a high of about 115° C., or about 120° C. This flashed forward stream comprises acetone and may comprise water cumene, AMS, and phenol. The line 208 can contain a low of about 60 vol %, or about 65 vol % to a high of about 70 vol %, or about 75 vol % acetone. The line 208 can contain a low of about 3.5 vol %, or about 4.0 vol %, to a high of about 5.0 vol %, or about 5.5 vol % cumene. The line 208 can contain a low of about 21 vol %, or about 23 vol % to a high of about 27 vol %, or about 29 vol % water. The line 208 can contain a low of about 0.3 vol %, or about 0.32 vol % to a high of about 0.38 vol %, or about 0.40 vol % AMS. The line 208 can contain a low of about 0.8 vol %, or about 1.0 vol % to a high of about 1.3 vol %, or about 1.5 vol % phenol. The flashed forward stream vapor stream 208 may be combined with the overhead stream 120 of the CAC 114. For example, stream 208 may be added to the feed to the APC 124 either upstream (208*a*) or downstream (208*b*) of the CAC condenser 118. Providing the flashed forward stream 208 upstream of the CAC condenser 118 (via stream 208*a*), or using another partial condenser (not shown), may reduce the phenol content of the net vapor stream before sending the stream to the APC 124. The CAC condenser 118 can by cooled by air, cooled by cooling water, cooled by tempered water, or cooled by the cumene feed stream to the oxidizer as described in U.S. Pat. No. 8,889,915.

Using a flash forward configuration, as illustrated in system 200 results in an increase in efficiency of the system. Specifically, by bypassing the CAC 114, some of the work of the CAC reboiler 116 is offloaded. For example, this improved process may lower the energy input to the CAC by 20% to 30%, for example by 25%, depending on operational parameters.

A further improvement in the system 200 relates to how a portion of acetone is recycled from the APC 124 back to the cleavage reactor(s). Recall from the discussion of the system 100 (FIG. 1) that a portion of purified acetone was recycled to the first stage cleavage reactor 104 via line 106. In the system 200 of FIG. 2, the recycle acetone (line 210) is taken as a side draw below the acetone product line 134. The inventors have recognized that the energy used in the top part of the APC is primarily consumed by the separation of acetone from water and other light impurities. The inventors have also recognized that purified acetone recycled from the reflux condenser 131 (as shown in FIG. 1) or from the product acetone draw 134 provides recycled acetone that is purer than it needs to be to facilitate the cleavage reactions. Thus, lowering the point on the column from which the recycled acetone is drawn provides a substantial savings of energy consumed by the APC 124. The distance DH below the product acetone draw from which the recycle acetone is drawn will be determined based on the particular implementation by balancing the energy savings (greater DH provides greater energy savings) and the required purity and/or dryness of the recycled acetone. Drawing the recycle acetone too low on the column risks contaminating the recycled acetone with caustic material, for example. It is within the ability of a person of skill in the art to determine the optimum location of the recycle acetone draw 210 for a particular implantation based on these considerations. As described above, the amount of acetone recycled to the cleavage reactor(s) may be determined as a ratio based on the feed of CHP to the cleavage reactor(s). For example, the ratio of recycled acetone to CHP feed may be about 0.1 to about 0.5 by weight.

As shown in the below table, the two improvements described herein, namely (1) flashing an acetone-rich portion of the cleavage product forward in the process so that the portion bypasses the CAC, and (2) obtaining recycle acetone from a side draw lower on the APC, each result in higher efficiency. Flashing an acetone-rich portion of the cleavage product forward in the process (Embodiment 1) increases efficiency of the process by reducing the energy that must be input to the CAC reboiler. Obtaining recycle acetone from a side draw lower on the APC (Embodiment 2) increases efficiency by reducing the energy that must be input to the APC reboiler. It should be noted that while the illustrated system 200 includes both of these embodiments, each embodiment individually contributes to gains in efficiency. Accordingly, processes and systems including either of the embodiments, alone or in combination, are within the scope of the disclosure.

A comparative study of the system 100 with the embodiments of the improved system 200 was done by process simulation. The CHP stream 102 to the first cleavage reactor 104 with about 82 wt % CHP and 18 wt % cumene was used as the feed stream for the study. In both systems, the flowrate of the recycle acetone to the first cleavage reactor 104 was kept the same. The comparative result of this study is shown in Table 1

TABLE 1

|  | System 100 | System 200 | Relative Energy reduction of System 200 over System 100 |
|---|---|---|---|
| CAC Reboiler 116 Duty | 100 | 75 | 25% |
| APC Reboiler 130 Duty | 33 | 23 | 30% |
| Total Energy Input | 133 | 98 | 26% |

The study indicates that the use of Embodiment 1 reduces the energy to CAC by 25% while the Embodiment 2 reduces the energy to APC 124 by 30%. The total energy reduction to the overall acetone processing system when both embodiments are implemented is about 26%.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of producing acetone, the method comprising:
   (i) cleaving cumene hydroperoxide (CHP) in at least one cleavage reactor to form a cleavage product stream,
   (ii) separating the cleavage product stream into an overhead stream and a bottoms stream,
   (iii) separating the bottoms stream in a crude acetone column to provide a phenol-rich stream and an acetone-rich stream,
   (iv) feeding both the overhead stream of step (ii) and the acetone-rich stream of step (iii) to an acetone product column, and
   (v) obtaining product acetone from the acetone product column.

2. The method of claim 1, wherein the at least one cleavage reactor comprises a first stage cleavage reactor and a second stage cleavage reactor, and wherein cleaving CHP comprises:
   providing the CHP to the first stage cleavage reactor,
   contacting the CHP with an acid catalyst, recycled acetone, and water to form a first stage cleavage reactor product,
   providing the first stage cleavage reactor product to the second stage cleavage reactor, and
   obtaining the cleavage product stream as effluent from the second stage cleavage reactor.

3. The method of claim 1, wherein separating the cleavage product stream into an overhead stream and a bottoms stream comprises flashing the cleavage product stream in a flash drum to provide the overhead stream from the flash drum.

4. The method of claim 3, wherein the flash drum operates at a pressure of about 90 kPa to about 190 kPa.

5. The method of claim 3, wherein the overhead stream from the flash drum comprises about 60 volume % to about 75 volume % acetone.

6. The method of claim 1, further comprising cooling the bottoms stream of step (ii).

7. The method of claim 1, further comprising neutralizing the bottoms stream of step (ii).

8. The method of claim 1, wherein feeding both the overhead stream of step (ii) and the acetone-rich stream of step (iii) to an acetone product column comprises combining the overhead stream of step (ii) with the acetone-rich stream of step (iii) to form a combined stream and feeding the combined stream to the acetone product column.

9. The method of claim 8, wherein the crude acetone column comprises a condenser and wherein combining the overhead stream of step (ii) with the acetone-rich stream of step (iii) comprises feeding the overhead stream of step (ii) to the condenser.

10. The method of claim 1, further comprising recycling recycle acetone from the acetone product column to a cleavage reactor that is used to perform step (i).

11. The method of claim 10, wherein the acetone product column comprises a first side draw from which the product acetone is obtained and a second side draw from which the recycle acetone is obtained.

12. The method of claim 10, wherein the second side draw is located below the first side draw.

13. A method of producing acetone, the method comprising:
    (i) cleaving cumene hydroperoxide (CHP) in at least one cleavage reactor to form a cleavage product stream,
    (ii) treating at least a first portion of the cleavage product stream to wash and neutralize the first portion of the cleavage product stream,
    (iii) separating the first portion of the cleavage product stream in a crude acetone column to provide a phenol-rich stream and an acetone-rich stream,
    (iv) feeding the acetone-rich stream of step (iii) to an acetone product column, and
    (v) obtaining product acetone from a first side draw of the acetone product column and obtaining recycle acetone from a second side draw of the acetone product column.

14. The method of claim 13, wherein the second side draw is below the first side draw.

15. The method of claim 13, wherein the at least one cleavage reactor comprises a first cleavage reactor and a second cleavage reactor.

16. The method of claim 15, further comprising recycling the recycle acetone to the second cleavage reactor.

17. The method of claim 16, wherein recycling the recycle acetone to the second cleavage reactor comprises recycling an amount of acetone that has a weight ratio of acetone to CHP of about 0.05 to about 0.25 based on the CHP provided to the at least one cleavage reactor.

18. The method of claim 13, further comprising, prior to step (ii), flashing the cleavage product in a flash drum to provide the first portion of the cleavage product stream as a bottom stream from the flash drum and to provide an overhead stream.

19. The method of claim 18, further comprising flashing the overhead stream forward downstream of the crude acetone column.

* * * * *